US007033173B2

(12) United States Patent
Coopersmith

(10) Patent No.: US 7,033,173 B2
(45) Date of Patent: Apr. 25, 2006

(54) GINGIVAL RETRACTION DEVICE AND METHOD

(76) Inventor: Allan Coopersmith, Hampsted 5757 Decelles Ave., Suite 520, Montreal, Quebec (CA) H3S 2C3

( * ) Notice: Subject to any disclaimer, the term of this patent is extended or adjusted under 35 U.S.C. 154(b) by 0 days.

(21) Appl. No.: 10/734,233

(22) Filed: Dec. 15, 2003

(65) Prior Publication Data

US 2004/0126740 A1    Jul. 1, 2004

Related U.S. Application Data

(63) Continuation of application No. pct/ca02/00910, filed on Jun. 17, 2002.

(60) Provisional application No. 60/298,201, filed on Jun. 15, 2001, provisional application No. 60/302,030, filed on Jul. 2, 2001.

(51) Int. Cl.
*A61C 9/00* (2006.01)
(52) U.S. Cl. ...................................... 433/136; 433/215
(58) Field of Classification Search ............... 433/136, 433/215, 40, 141, 138, 139
See application file for complete search history.

(56) References Cited

U.S. PATENT DOCUMENTS

| 3,151,393 | A | * | 10/1964 | Holmes ........................ 433/40 |
| 3,238,620 | A | * | 3/1966 | Robertson .................... 433/40 |
| 3,541,689 | A | * | 11/1970 | Snead .......................... 433/40 |
| 4,321,038 | A | * | 3/1982 | Porteous ..................... 433/136 |
| 4,396,375 | A | * | 8/1983 | Gores .......................... 433/141 |
| 4,465,462 | A | * | 8/1984 | Ticknor ....................... 433/136 |
| 4,617,950 | A | | 10/1986 | Porteous et al. |
| 4,677,139 | A | | 6/1987 | Feinmann et al. |
| 4,871,311 | A | * | 10/1989 | Hagne ......................... 433/136 |
| 4,892,482 | A | | 1/1990 | Lococo |
| 4,930,920 | A | | 6/1990 | Fitzig |
| 5,022,859 | A | * | 6/1991 | Oliva .......................... 433/141 |
| 5,213,498 | A | | 5/1993 | Pelerin |
| 5,362,495 | A | | 11/1994 | Lesage |
| 5,480,303 | A | * | 1/1996 | Groth .......................... 433/136 |
| 5,540,588 | A | * | 7/1996 | Earle ........................... 433/136 |
| 5,676,543 | A | | 10/1997 | Dragan |
| 5,899,694 | A | * | 5/1999 | Summer ....................... 433/136 |
| 6,116,905 | A | | 9/2000 | Hoos |
| 6,170,714 | B1 | | 1/2001 | Lesage |
| 2004/0265777 | A1 | | 12/2004 | Heasley |
| 2005/0008583 | A1 | | 1/2005 | White |
| 2005/0069838 | A1 | | 3/2005 | Kollefrath |

FOREIGN PATENT DOCUMENTS

| CA | 2441907 | | 12/2003 |
| DE | 31 22 834 | * | 12/1982 |
| DE | 3122834 A | | 12/1982 |

(Continued)

OTHER PUBLICATIONS

Copy of International Search Report Dated Sep. 23, 2002 in PCT/ CA02/00910.

*Primary Examiner*—Ralph A. Lewis

(57) ABSTRACT

A device for retracting gingival tissue away from a tooth comprising a preformed integral closed loop of material sized and dimensioned to be packed into a sulcus associated with the tooth, the closed loop having an inner surface suitable for placement against the at least one tooth and an outer surface suitable for placement against gingival tissue. The loop is preferably deformably rigid, extensile and non-elastic. The material is preferably compressible and absorbent. The device may also comprise several such loops linked together at their periphery to form a unitary structure. A method of use these devices is also disclosed.

8 Claims, 6 Drawing Sheets

FOREIGN PATENT DOCUMENTS

| | | | | | |
|---|---|---|---|---|---|
| DE | 9211339 U1 | 11/1992 | FR | 2761591 * | 10/1998 |
| DE | 29912502 U1 | 2/2000 | FR | 2761591 A1 | 10/1998 |
| DE | 299 12 502 * | 3/2000 | WO | WO 02/102269 * | 12/2002 |

\* cited by examiner

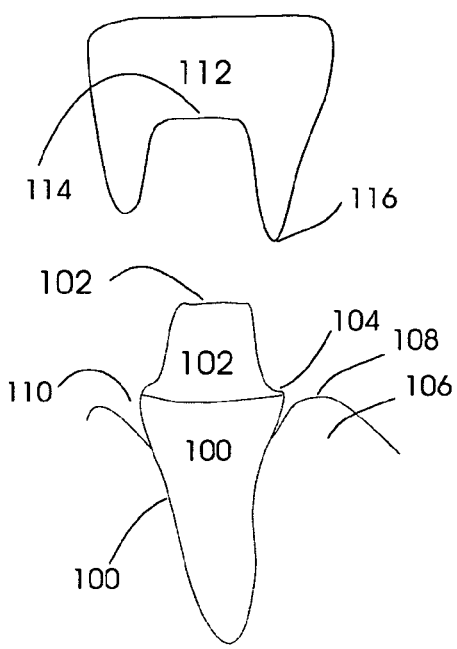
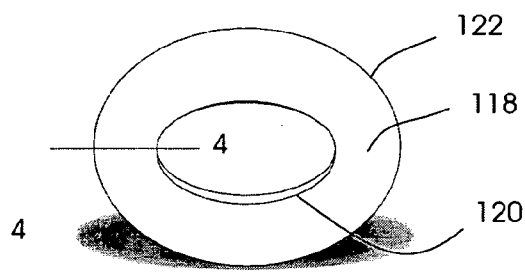
Fig. 2
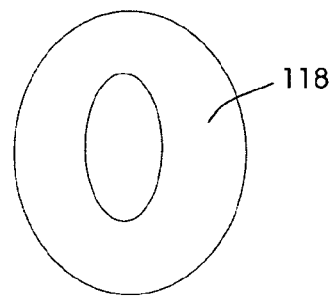
Fig. 3
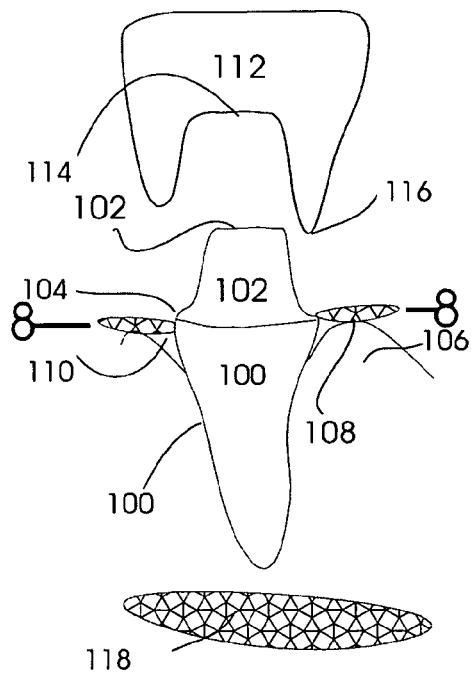
Fig. 4
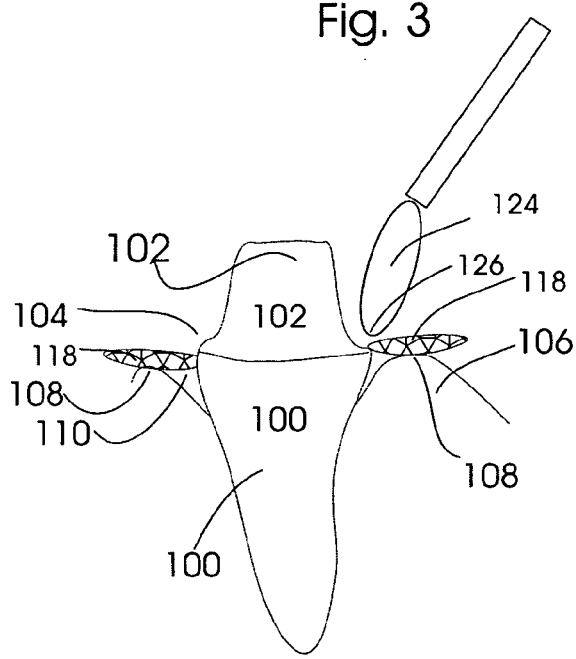
Fig. 5

GINGIVAL RETRACTION DEVICE AND METHOD

The present application is a continuation of International Patent Application serial no. PCT/CA02/00910 filed Jun. 17, 2002, now pending as to the designation of the United States of America. Through that application this application claims the benefit of U.S. Provisional Patent Applications Ser. No. 60/298,201 entitled "Gingival Retraction Device and Method" filed Jun. 15, 2001 and Ser. No. 60/302,030 entitled "Retractowedge Gingival Retraction Device" filed Jul. 2, 2001. The contents of all three of these applications are incorporated herein by reference.

FIELD OF THE INVENTION

This invention relates to apparati and methods employed by dental practitioners to retract gingival tissues from around the base of a tooth, to control oral bleeding and provide gingival tissue fluid control, such as for a tooth which has been prepared by drilling or other means to receive a dental restoration, such as a crown or inlay.

BACKGROUND OF THE INVENTION

Around each healthy tooth in the mouth of a human is a narrow groove termed a sulcus, which separates the tooth from the surrounding gingival tissue at the surface of the tissue. Certain dental procedures, such as those to create an impression of the tooth and those to create a prosthetic for the tooth, require that the gingival tissue be retracted from the tooth in the area of the sulcus. While the prior art teaches several means of accomplishing this retraction, none is optimal.

One commonly employed conventional method is through the use of retraction cord. Simply described, retraction cord is length of cord that is wrapped around the base of the tooth several times and then manually forced into the sulcus by a dental practitioner. The manual force will cause the gingival tissue to separate from the tooth and the presence of the cord will prevent the tissue from returning to its original state. Unfortunately, the use of retraction cord has several drawbacks. First, the cord is typically supplied by manufacturers wound on a spool, packed into a container. To use the cord, the dental practitioner must estimate the amount required for the particular application. Since the cord must be wrapped around to tooth while the ends are held in one hand by the practitioner, a significant amount of cord is wasted in the process. Second, it is very difficult to force and maintain the cord within the entire sulcus (around the entire circumference of the tooth) at the same time. It is very common for the force required to insert the cord into one area of the sulcus to cause cord already inserted to other areas of the sulcus to exit the sulcus. This requires the practitioner to repack those areas causing tearing and abrasion of the inner lining of the sulcus, leading to bleeding and/or exuding of crevicular fluid, which may cause contamination and/or inaccuracies in the dental procedures to be performed. Third, inherent in the process is that the cord does not conform well to the various depths and widths of the sulcus nor the irregularities of any prepared tooth margins. Finally, the entire process is relatively time consuming.

Another type of retraction cord is made of strands of a fiber such as cotton stiffened with a stiffener strand such as for example a copper wire threaded through the core of the cord. The stiffener is made of material that provides the cord with deformability. Positioning of this type of the cord over the whole periphery of the tooth is delicate. In addition, because of the stiffener strand, this process is relatively painful and generally requires a local anesthesia. Moreover as one end of this stiffened strand is packed into the sulcus, the other end tends to become displaced out of the sulcus. A frequent lesion is observed of the epithelial attachment as well as hemorrhages or oozing upon withdrawal of the cord. In addition, this type of cord suffers from some of the other above-noted drawbacks associated with retraction cords.

A second commonly employed method is through the use of an injectable paste. In this method a relatively large needle is placed in the sulcus and is used to inject a biocompatible paste therein under relatively high pressures (between 13,000 and 30,000 Pascals). This method too has several disadvantages. Typically, either the needle itself or the paste injected under high pressure or both cause trauma to the gingival tissue. Moreover, the paste does not adhere well to moist tissues and typically is displaced out of the sulcus. Because of the high pressures involved, the paste injection device (commonly termed a "gun") is complicated, expensive and suffers frequent breakdowns (as does the actual paste container).

A third conventional method is the use of a pressure cap. A pressure cap is a cap made of a spongy material that is fitted around the tooth and causes retraction of the gingival tissue through the application of pressure. The difficulty here is that the shape of the cap is even and constant while that of the sulcus (depth and width) is not. Therefore this method is imprecise and does not ensure accurate nor sufficient retraction. For these reasons, it is presently only used to ensure haemostatis after a procedure of gingival eviction (described below).

An additional convention method is termed gingival eviction. In this method the gingival tissue is retracted by electric bistoury, laser, or by a diamond charged drill ("diamond curretage"). None of these procedures, however, is not without its drawbacks. Electric bistoury and laser generally mutilate the gingival tissue and are therefore quite painful and require local anesthesia. Similarly diamond curretage is also quite painful and causes prolific bleeding. Each of these procedures is traumatic and creates gingival shrinkage and recessions leading to undesirable unprotected root coverage.

There is therefore a need in the art for an improved apparatus for, and method of, retracting gingival tissue from a tooth, which are preferably more efficient and less traumatic than conventional methods.

SUMMARY OF THE INVENTION

It is therefore an object of an aspect the present invention to provide an improved apparatus for retracting gingival tissue from a tooth.

It is a further object of an aspect of the present invention to provide an improved method for retracting gingival tissue from a tooth.

In one aspect, as embodied and broadly described herein, the present invention provides a device for retracting gingival tissue away from at least one tooth, the device comprising a preformed integral closed loop of material sized and dimensioned to be packed into a sulcus associated with the at least one tooth, the closed loop having an inner surface suitable for placement against the at least one tooth and an outer surface suitable for placement against gingival tissue.

A tooth may be prepared for dental procedure via conventional methods to create a tooth abutment having a tooth margin. The margin may be described as a small shelf like area extending from the tooth abutment to the edge of the tooth in the area of the gumline. Generally, the tooth is prepared such that the sulcus is located axially outward from the tooth margin. In order to perform further dental procedures on the tooth, the sulcus must be enlarged such that the gingival tissue is further away from the tooth margin.

The closed loop of the material of the present invention is used for this purpose. The loop is prefabricated to be of a size and dimension allowing it to be placed over the tooth in the area of the margin and to be packed (forced) into the sulcus using conventional dental instruments. This packing causes axial and apical pressure on the gingival tissue causing it to retract away from the tooth margin. Moreover this pressure is even and steady around the entire circumference of the tooth.

The present invention overcomes the deficiencies of the prior art in several respects. Because the closed loop is correctly sized to fit into the sulcus, portions of the closed loop that have already been packed into the sulcus are generally not forced out as subsequent areas of the closed loop are packed. Thus, packing of the sulcus in the same area several times, and the tearing and/or abrasions associated therewith are minimized or avoided. Mutilation of the gingival tissue is avoided. Further because of their correct size and fit within the sulcus, the loops cannot be easily accidentally dislodged by the patient's tongue or cheek or other dental instruments such as suction tubes.

Moreover, the loops of the present invention are easy to handle and to place, are inexpensive, are easy to sterilize and may be easily individually packaged to retain their sterility. They may be disposable. Finally, the loops of the present invention allow for faster, more accurate and less damaging gingival retractions, leading to better results from the dental procedures (e.g. preparing a crown) that they are intended to facilitate.

As used in the context of the present specification, the term "closed loop" is intended to include any ring-like structure, whether circular or otherwise in shape when viewed from above. As a non-limiting examples, the closed loop may be circular, elliptical, oval, square, rectangular, triangular, polygonal, or irregular in shape when viewed from above. A closed loop of the shape of the tooth (in the tooth margin area) over which the closed loop is intended to be placed is preferred.

Similarly, the closed loop of the present invention is not intended to be restricted to one having any particular cross-section. Loops having all types of cross-sections are believed to be within its scope. As non-limiting examples, the cross-section of the loop may be circular, elliptical, oval, square, rectangular, polygonal, heart, boomerang, wishbone or irregular in shape when viewed from above. A triangular, wedge-shaped or modified wedge-shaped cross-section is preferred as either of these allow for easier packing of the loop into the sulcus as these shapes more accurately conform to the shape of the sulcus and more effectively transfer the occlusal or manual pressure into axial self-retention of the device and lateral retraction of the gingival tissue. Further, it should be understood that it is not necessary that the loop of the present invention have a single cross-section over its entire length. While uniformity in the cross-section of the loop over its entire length is preferred, it is not required.

The loop is sized and dimensioned to allow it to be easily packed into the sulcus of a tooth. It should be understood that since each human has several different types of teeth, each being of different size, and that since the size of the same type of tooth will vary between humans, there are closed loops of the present invention of many sizes and shapes. Indeed, it is contemplated that, in commercial use, several different sizes and shapes of closed loops of the present invention will be sold.

It is preferred that the loop be substantially flat; the uppermost points on its upper surface should be co-planar as should the lowermost points on its lower surface.

It is highly desirable that the closed loop of the present invention have no breaks in the structure of the loop around its length, i.e. the loop is completely annular. However, it is contemplated that a loop having a slight break (and thus being penannular) would be with in the scope of the present invention, provided that the break is small enough that the functionality of the loop would not be materially affected. It is also contemplated that where there is a slight break, the ends of the loop may overlap slightly.

The loop of the present invention is preformed. The dental practitioner (or others working with him) does not cause the material comprising the loop to actually assume the shape of a closed loop during the course of the dental procedure in which the loop will be used. The loop is also integral; it is a single whole structure that is originally created as such. I.e. the device is originally manufactured having a loop, it is not manufactured as a linear length of material that is wrapped around to form a loop at the time of use.

It is highly preferable that the loop be deformable. The shape of the loop should be able to be altered by the force exerted thereon used to pack the loop into the sulcus. Deformability is highly desirable as (depending on the method of manufacture of the loop) it is highly unlikely that the loop will be formed in a shape that registers perfectly with the outer surface of the tooth at the tooth margin. It is much more likely that small alterations in the shape of the loop will be necessary in order to provide the loop with the shape of the circumference of the tooth while packing it into the sulcus. As part of its deformability the loop may need to be extensile to accommodate being placed over a tooth having a circumference greater than the initial interior circumference of the loop. The loop, however, should be resistant to tearing while being deformed and should also be non-elastic. Once deformed it should retain its new shape. It should not tend to return to its original pre-deformation shape because this impedes gingival tissue retraction.

Further, it is highly preferable that the loop be deformably rigid. In order that the loop be easy to work with before its insertion into the sulcus, the loop should retain its shape (not deform) under forces less than the amount necessary to pack it into the sulcus. In this manner, the loop will be able to be removed from whatever shipping, packing, and/or storage material in which it is located; handled by the dental practitioner; and placed into the mouth of the patient over the tooth, all without deforming.

The material(s) of which the loop is constructed preferably is (are) one (or more) selected from the group consisting of thread, paper, blotter, sponge, gel, jelly, foam, cellulose, polyvinylsiloxane, silicone, plastic, paste. More preferably, the material is a mixture of cotton fibres. Still more preferably, the material is a mixture of cotton fibres (75%) and polyester fibres (25%), similar to that found in readily available commercial absorbent products such as sanitary napkins and diapers. For simplicity and ease of use and manufacture it is preferred that the material consists essentially of a single material, or more preferably a mixture of two materials. Where the loop comprises more than one material, it may comprise either a homogenous mixture of materials or separate and distinct layers of different materials or mixtures of homogenous materials. In such cases is it preferred that the loop comprise a thin layer of a fluidimpervious material (e.g. akin to the barrier layer of a conventional sanitary napkin), and an absorbent layer (e.g. the mixture of cotton and polyester fibres described hereinabove).

It should be understood that the loop may be soaked or otherwise impregnated with or otherwise contain or carry other medical ingredients without departing from the scope of the present invention. By way of non-limiting example, such ingredients may be astringents, antiseptics, antibiotics, and hemostyptics. For the purposes of the present specification, such additional medical ingredients should be ignored in determining the composition of the material that comprises the loop.

The loops of the present invention may be manufactured by any conventional means appropriate for the materials of which they are constructed. As a non-limiting example, the loops may be formed by creating a web of material (such as an absorbent cotton or cotton/polyester mixture) and stamping or die-cutting the loops therefrom. In such cases the methods of manufacture are similar to those of conventional sanitary napkins and/or diapers. The previous described web of material may comprises several different types of layers. By way of non-limiting example, the layers may be a fibrous layer, a paste layer, and gelatinous layer.

Whatever the composition of the material, it is preferred that the material be compressible in use. The material should be able to be compacted while the loop is being packed into the sulcus, and in this manner, the material will be under pressure once forced therein. The pressure caused by the compressed state of the material will aid in forcing the sulcus to expand and retracting the gingival tissue. It also desirable that the material be absorbent so that fluids being exudated from the body into the sulcus are contained and maintained away from the tooth where they could negatively interfere with the dental procedures to be performed. Further absorbent materials generally tend to increase in size as they absorb, thus in the present case, increasing the amount of pressure on the gingival tissue and thereby the retraction.

In addition, it is highly preferred that the material be atraumatically removable from the sulcus. Ideally, the material should not have any component that bonds to either the gingival tissue or the tooth making removal of the loop difficult or causing damage to either. Ideally, the loop should be able to be removed from the sulcus as simply as it was inserted via being pulled out by a conventional dental instrument. It should deform as appropriate so as not to cause trauma to the patient.

In another aspect, as embodied and broadly described herein, the present invention provides a method of preparing a tooth for a dental procedure comprising the steps of: removing a portion of a tooth to create a tooth abutment; placing a loop as described hereinabove around the tooth abutment; and packing the loop into a sulcus associated with the tooth. Unless it is biodegradable or soluble, the loop should be removed from the sulcus at the appropriate point in the procedure.

Each of these steps can be accomplished through the use of conventional dental instruments, and thus it is believed that a detailed description thereof is necessary for a dental practitioner to practice the claimed invention.

In a preferred embodiment, once the tooth has been prepared to create a tooth abutment, a provisional restoration is prepared (both by conventional methods). As opposed to the dental practitioner simply manually packing the loop into the sulcus, once the loop has been placed around the tooth abutment, the provisional restoration is placed on top of the loop which is resting in the area of the sulcus, and the patient is instructed to bite down on the provisional restoration. The occlusal pressure thus exerted will cause the loop to be forced into the sulcus all around the tooth nearly simultaneously and to conform to the irregularities of the prepared tooth margin. Should the patient have no tooth opposing the provisional restoration a relatively large cotton wad may be placed thereon (enabling the patient to bite down) or alternatively, the dental practitioner may apply manual pressure.

In a most preferred embodiment, again, once the tooth has been prepared to create a tooth abutment, a provisional restoration is prepared. The loop is then releasably adhered to the gingival margin, and the provisional restoration (having the loop adhered thereto) is placed on the tooth and the patient is instructed to bite down on the provisional restoration. The occlusal pressure thus exerted will cause the loop to be forced into the sulcus all around the tooth nearly simultaneously. Any mild adhesive will suffice for this purpose. One example is the material sold under the trademark Caulk Tray Adhesive by Dentsply International Inc. of Milford, Del., USA.

In either of the above methods, before the patient bits down, optionally, a piece of cotton or other similar fiber may be placed on top of the provisional restoration, to aid in the process. Further, it is also possible for the dental practitioner to manually pack the loop into the sulcus after on of the non-manual packing methods described above have been employed, should additional packing be desired or required. Finally, there is an additional benefit in that in many situations a portion of the loop will remain trapped between the provisional restoration and the tooth margin (while the majority is packed into the sulcus). This being trapped aids in anchoring the loop in place and preventing it from exiting the sulcus, either by the patient (by accident) or the dental practitioner (during additional manual packing of the loop, for example).

For ease, convenience, simplicity and efficiency, in any of the above methods, before the loop is placed into the mouth of the patient, conventional injection paste may be applied to the loop. As was previously described hereinabove, injection paste when used under conventional methods tends to exit the sulcus. The present invention has the additional benefit that if the paste is applied to the loop, and the loop packed into the sulcus, the loop itself will impede the paste from exiting the sulcus. In addition the extra-oral nature of the process, means that the application of the paste may be performed by a dental auxiliary and that no expensive or traumatic equipment need be used.

In the above paragraphs, the present invention has been described in terms of a single tooth. It is, however, within the scope of the present invention that a retraction device be constructed for use with more than one tooth. Thus, as embodied and broadly described here, the present provides a device for retracting gingival tissue away from a plurality of teeth, the device comprising a plurality preformed integral closed loops of material sized and dimensioned to be packed into a sulcus associated with the teeth, each of the closed loops having an inner surface suitable for placement against one of the plurality of teeth and an outer surface suitable for placement against gingival tissue.

In this aspect a plurality of the loops described hereinabove are attached to one another at their periphery to form a somewhat chain-like unitary structure. This structure may be used when one more than one tooth is being prepared for a dental procedure. The dental practitioner simply takes the structure and places one loop around one tooth. He then works tooth by tooth packing each loop into the sulcus associated with its tooth until all of the loops have been packed. Removal of the device is simply the reverse of this process.

Other objects and features will become apparent by reference to the following description and the drawings.

DESCRIPTION OF THE DRAWINGS

A detailed description of preferred embodiments of the claimed invention is provided hereinbelow, with reference to the following drawings, in which:

FIG. 1 is a longitudinal cross-sectional view of a human tooth and a provisional restoration;

FIG. 2 is a perspective view of a first embodiment of the present invention;

FIG. 3 is a planar cross-section of the embodiment shown in FIG. 2 taken along the line 3—3;

FIG. 4 is a perpendicular cross-section of the embodiment shown in FIG. 2 taken along the line 4—4;

FIG. 5 is a longitudinal cross-sectional view of a human tooth as in FIG. 1 illustrating the manual packing of a first embodiment of a device of the present invention into a sulcus;

Figure 6:
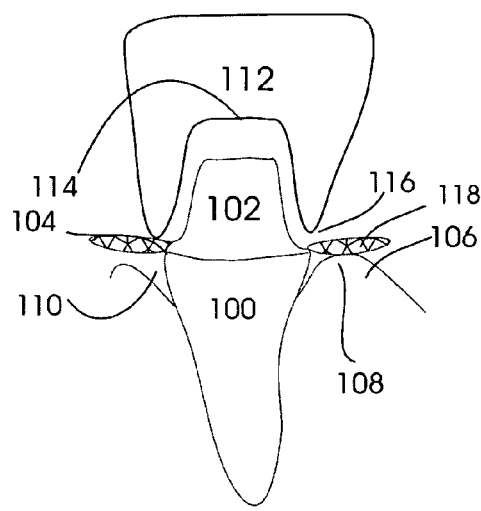
FIG. 6 is a longitudinal cross-sectional view of a human tooth as in FIG. 1 illustrating the packing of a first embodiment of a device of the present invention into a sulcus via a provisional restoration.

In the drawings, preferred embodiments of the invention are illustrated by way of example. It is to be expressly understood that the description and drawings are only for purposes of illustration and as an aid to understanding, and are not intended to be a definition of the limits of the invention.

DETAILED DESCRIPTION OF PREFERRED EMBODIMENTS

Referring to FIG. 1 there is illustrated a human tooth 100 that has been prepared for a dental procedure by conventional means. Specifically the surface tooth structure of the tooth 100 has been removed creating a tooth abutment 102 having a tooth margin 104. The tooth 100 is embedded in gingival tissue 106 having a gingival crest 108. Between the gingival tissue 106 and the tooth 100 is located a sulcus 110.

A provisional restoration 112 has been fabricated by conventional means from a dental impression to register with the prepared tooth 100. The provisional restoration 112 has an interior surface 114 and a margin 116 that are together configured to conform to the tooth abutment 102 and the tooth margin 104. As can be seen in the drawings the preparation of the tooth 100 and thus the provisional restoration 112 may not be symmetric about the center of the tooth 100.

Referring to FIG. 2, there is shown a first embodiment of closed loop 118 of the present invention. The loop 118 has an inner surface 120 suitable for placement against the outer surface of a tooth and an outer surface 122 suitable for placement against gingival tissue. As shown in FIGS. 3 and 4, the loop 118 is generally elliptical both in planar cross-section and in perpendicular cross-section. The loop 118 has been created by having been cut from a wet-laid web of 75% cotton fiber and 25% polyester fiber. The loop 118 has outer length of 11 mm and width of 9.5 mm. The loop has an inner length of 9 mm and a width of 7.5 mm.

Referring to FIG. 5, the loop 118 has been placed around the tooth abutment 102 with a dental tweezers (not shown). In this particular embodiment, owing to its size elliptical shape, the loop 118 does not immediately fall into the sulcus 110, but rather rests on the tooth margin 104 and the gingival crest 108. The loop 118 is sized and dimensioned to be packed into the sulcus 110, and FIG. 5 illustrates a conventional dental instrument, a plastic instrument, 124 that may be used for that purpose. To pack the loop 118 the dental practitioner (not shown) simply places the end 126 of the dental instrument 124 against a portion of the upper surface 128 of the loop 118 and applies pressure. Once that portion of the loop 118 has been packed into the sulcus 110, the practitioner proceeds to apply pressure to an adjacent section of the loop 118. This process continues until the entire loop 118 has been packed into the sulcus 110. The arrows (unnumbered) in FIG. 5 are meant to illustrate first the movement of the loop 118 into the sulcus 110, and the retraction of the gingival tissue 106 as a result.

Figure 7:
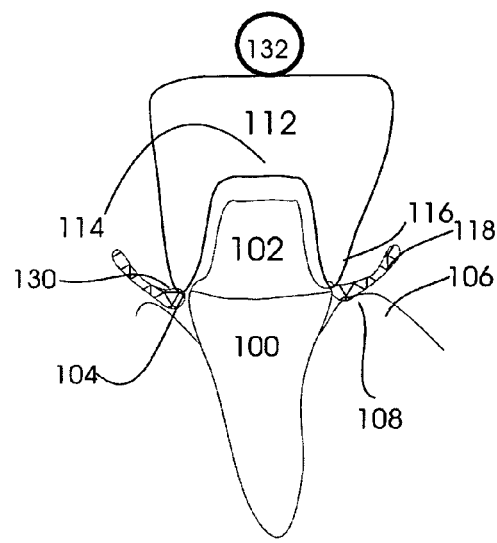
FIG. 7 is a longitudinal cross-sectional view similar to FIG. 6.
Figure 8:
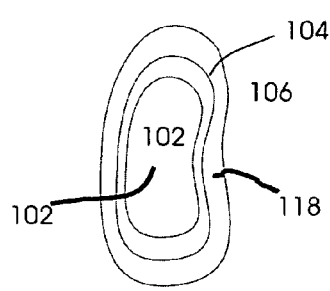
FIG. 8 is a transverse cross-sectional view taken along the line 8—8 in FIG. 7.

Referring to FIG. 6., there is shown another method of packing the loop 118 into the sulcus 110. In this method, the provisional restoration 112 is shown being placed onto the tooth abutment 102 so as to rest on the loop 118. The patient is then asked to bite down on the provisional restoration 112, and as shown in FIG. 7 and in cross-section in FIG. 8, the occlusal force exerted by the patient causes the loop 118 to be packed into the sulcus 110 nearly simultaneously around the entire circumference of tooth 100. In doing so, it is possible (as is shown in FIG. 7) that a portion 130 of the loop 118 will remain trapped between the provisional restoration margin 116 and the tooth margin 104. This trapped portion 130 serves to anchor the loop 118 and prevent it from being displaced from the sulcus 110. A piece of cotton 132 may be optionally placed on the tooth 100 before the patient is instructed to bite down.

Figure 10:
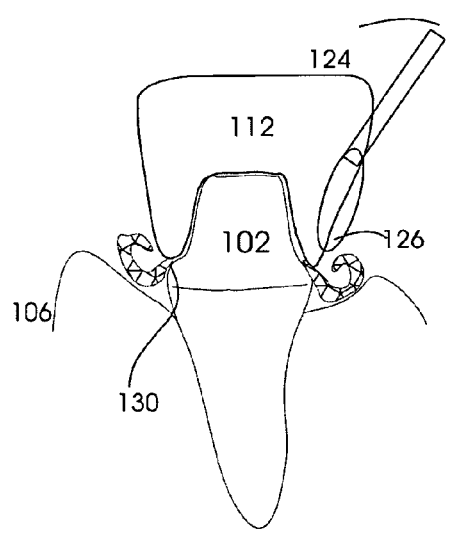
FIG. 10 is a longitudinal cross-sectional view similar to FIG. 9.
Figure 9:
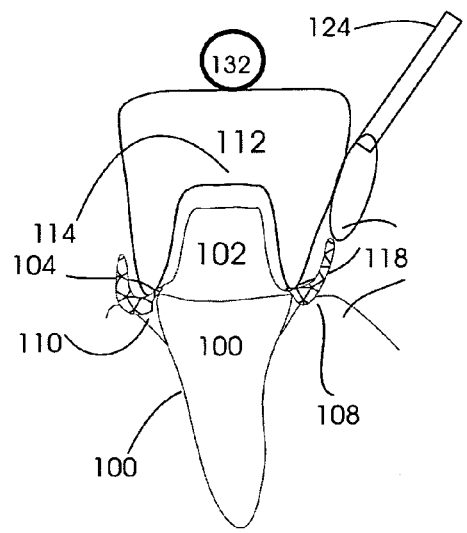
FIG. 9 is a longitudinal cross-sectional view similar to FIG. 6 illustrating additional manual packing of a first embodiment of a device of the present invention into a sulcus.

As shown in FIGS. 9 and 10, if the retraction of gingival tissue 106 is insufficient after the provisional restoration 112 has caused the loop 118 to be packed in the sulcus 110, or if for some reason a portion of the loop 118 will otherwise interfere with the dental procedure, the practitioner may cause additional packing through the application of manual force on the loop 118 via a dental instrument 124. This will cause more of the loop 118 to be packed in the sulcus 110 providing additional retraction.

Figure 11:
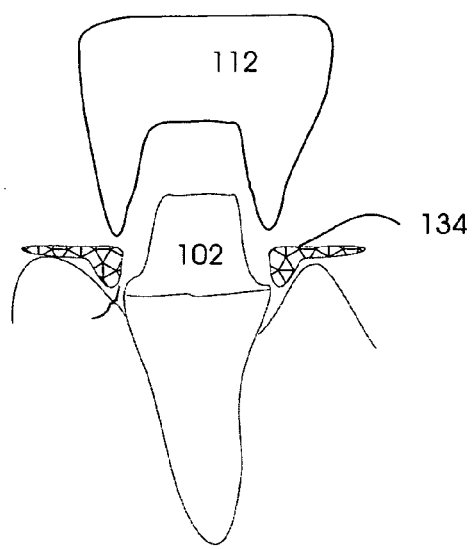
FIG. 11 is a longitudinal cross-sectional view of a human tooth, a second embodiment of a device of the present invention, and a provisional restoration.
Figure 12:
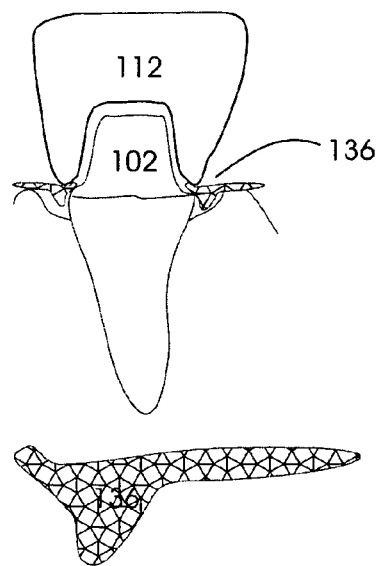
FIG. 12 is a longitudinal cross-sectional view of a human tooth, a third embodiment of a device of the present invention, and a provisional restoration.
Figure 13:
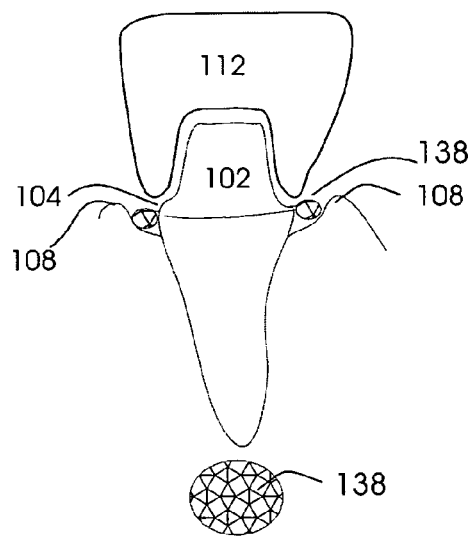
FIG. 13 is a longitudinal cross-sectional view of a human tooth, a fourth embodiment of a device of the present invention, and a provisional restoration.
Figure 14:
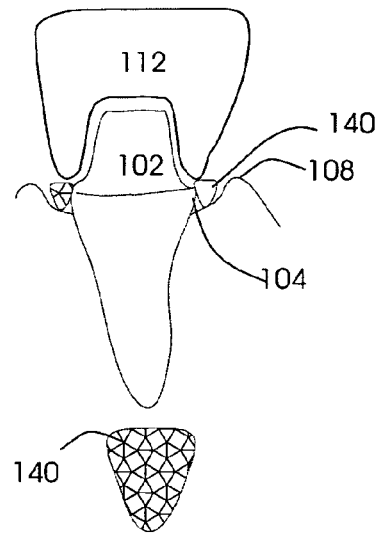
FIG. 14 is a longitudinal cross-sectional view of a human tooth, a fifth embodiment of a device of the present invention, and a provisional restoration.

Referring to FIGS. 11, 12, 13, 14, additional embodiments of the present invention, comprising loops of differing shapes are also possible. FIGS. 11 and 12 illustrate respectively a second embodiment wherein a loop 134 has a wedge shape in perpendicular cross-section and a third embodiment wherein a loop 136 has a modified (i.e. not a perfect) wedge shape in perpendicular cross-section. FIGS. 13 & 14 illustrate respectively a fourth embodiment wherein a loop 138 has a circular shape in perpendicular cross-section and a fifth embodiment wherein a loop 140 has a triangular shape in perpendicular cross-section. It should be noted that because of their shape and size, the circular shaped loop 138 and triangular shaped loop 140 do not need to rest on the tooth margin 104 and/or gingival crest 108, but may be placed (before being packed) directly into the sulcus 110. Such may be the case where the difference between the inner and outer surfaces is approximately 1 mm.

Figure 15:
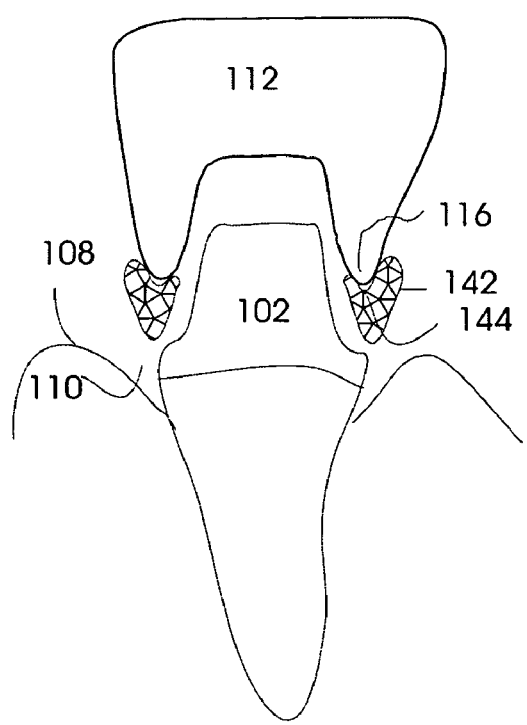
FIG. 15 is a longitudinal cross-sectional view of a human tooth and a sixth embodiment of a device of the present invention releasably adhered to a provisional restoration.
Figure 16:
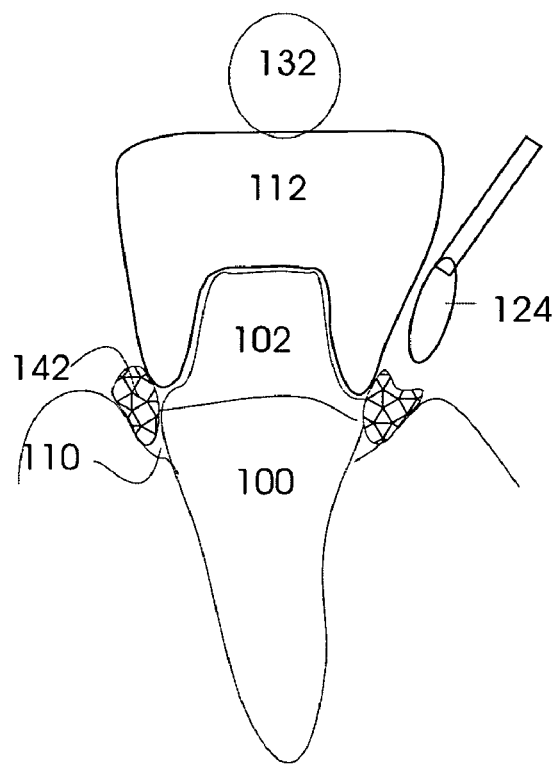
FIG. 16 is a longitudinal cross-sectional view similar to FIG. 16 illustrating additional manual packing of the device into the sulcus.

Referring to FIGS. 15 & 16 there is shown a sixth embodiment of the present invention, a loop 142 having a heart-shape in cross section. These figures further illustrate an additional method of use of the device. In this method, instead of being placed over the tooth abutment 102, the loop 142 is releasably adhered to the margin 116 of the provisional restoration 112 outside of the mouth of the patient with adhesive 144. The provisional restoration 112 having the loop 142 adhered thereto is then placed in the mouth of the patient over the tooth abutment 102. A piece of cotton 132 may then be placed on the provisional restoration 112 and the patient is asked to bite down. The occlusal pressure will almost simultaneously pack the loop 142 into the sulcus around the entire circumference of the tooth 100. Manual pressure may be supplied by a dental instrument 124 to additionally pack the loop 142 into the sulcus 110. After retraction, immediately prior to impression taking, the provisional restoration 112 can be easily removed bringing with it the loop 142 thereby easily and atraumatically withdrawing the loop 142 from the sulcus 110.

Figure 17:
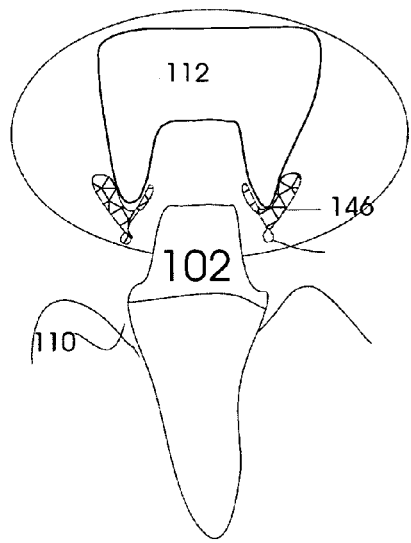
FIG. 17 is a longitudinal cross-sectional view of a human tooth and a seventh embodiment of a device of the present invention releasably adhered to a provisional restoration.
Figure 18:
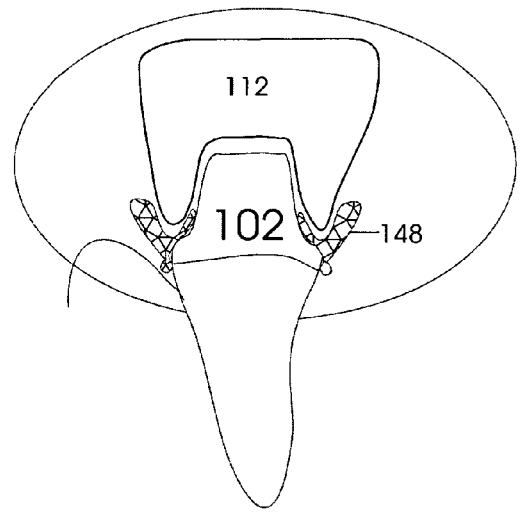
FIG. 18 is a longitudinal cross-sectional view similar to FIG. 18, shown with the provisional restoration packing the device into the sulcus.
Figure 19:
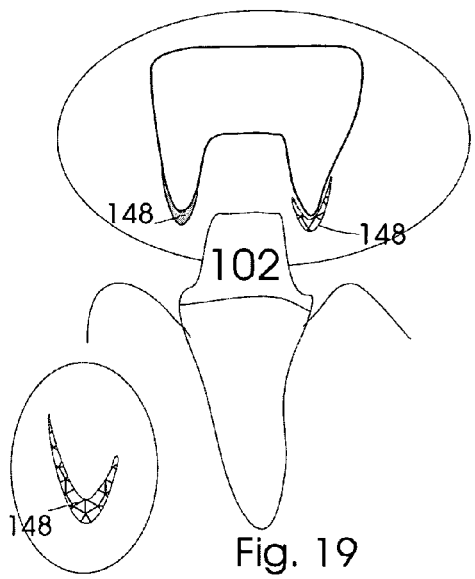
FIG. 19 is a longitudinal cross-sectional view of a human tooth and an eighth embodiment of a device of the present invention releasably adhered to a provisional restoration.
Figure 20:
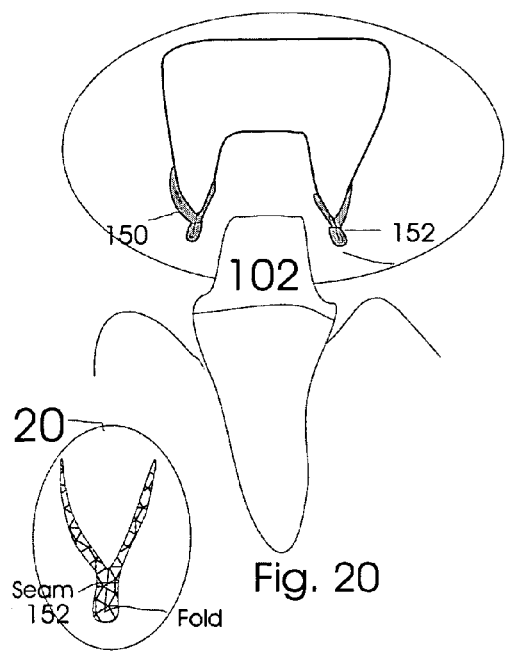
FIG. 20 is a longitudinal cross-sectional view of a human tooth and a ninth embodiment of a device of the present invention releasably adhered to a provisional restoration.

FIG. 17 illustrates a seventh embodiment of the present invention wherein the loop 146 has a wishbone shape in cross-section. As shown in FIG. 18, the loop 146 may be inserted into the sulcus 110 using the method of releasable adherence to a provisional restoration 112, as described above. Similarly, FIG. 19 illustrates an eight embodiment of the present invention wherein the loop 148 has boomerang shape in cross-section.

FIG. 18 illustrates a ninth embodiments wherein the loop 150 also has a wishbone shape in cross-section. Unlike the loop 146, however, the loop 150 is not formed as a wishbone, but is rather formed as a flat disk and then bent into a wishbone shape and secured together at seam 152.

Figure 21:
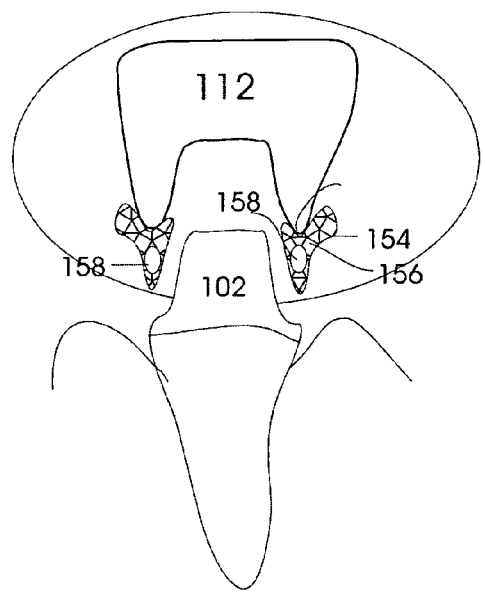
FIG. 21 is a longitudinal cross-sectional view of a human tooth and a tenth embodiment of a device of the present invention releasbly adhered to a provisional restoration.

The loops of the preceding embodiments are all generally constructed from a single material or a homogenous mixture of materials. Referring to FIG. 21, in a tenth embodiment is all possible to construct a loop 154 made of two different materials or homogenous mixtures of materials. As an example, the loop 154 has outer material 156 and an inner core of material 158. The outer material 156 is a wet-laid mixture of cotton and polyester fibres and the inner core material 158 is a dry, compressed sponge. The inner core material 158 could also comprise a number of conventional dental pastes.

Figure 22:
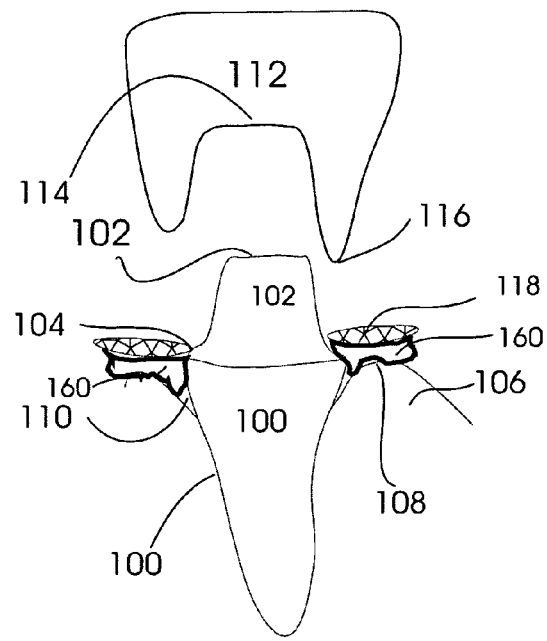
FIG. 22 is a longitudinal cross-sectional view of a human tooth similar to FIG. 6 (illustrating the first embodiment of a device of the present invention), showing the use of injection paste with the device.

FIG. 22 illustrates the use of conventional injection paste 160 with the present invention. Injection paste 160 is applied to a loop (as an example of the first embodiment) 118 outside of the mouth of the patient. The loop 118 is then placed into the mouth of the patient around the tooth abutment 102 with the injection paste 160 facing the sulcus 110. The pressure used to pack the loop 118 into the sulcus 110 (however applied) will also force the injection paste 160 into the sulcus 110. However, in the present case, owing to a gasket effect created by the loop 118 the injection paste 160 cannot exit the sulcus 110. This also provides the advantage that the paste 160 is compressed more effectively into the sulcus 110, more accurately confirming to the irregularities of the margin 104 thereby creating more effective and reliable gingival retraction.

Figure 23:
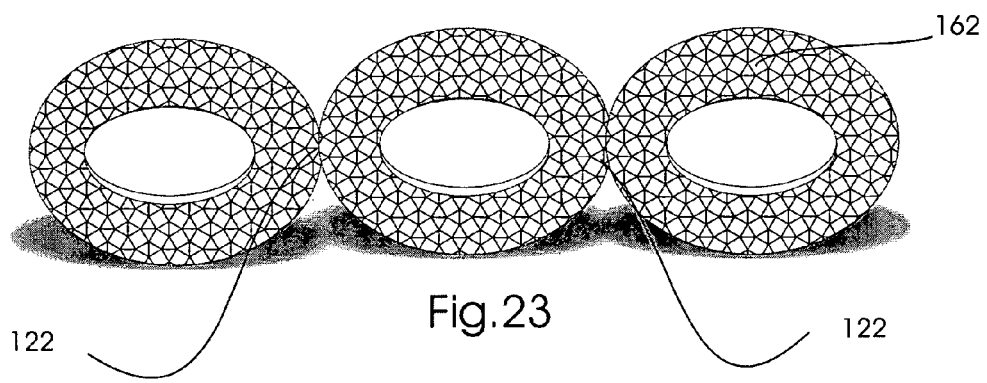
FIG. 23 is a perspective view of an eleventh embodiment of a device of the present invention suitable for use with a plurality of teeth.

Finally, FIG. 23 illustrates an eleventh embodiment of the present invention that may be used for multiple teeth. The device 162 has a plurality of loops (which may for example be any of those described above or a combination thereof or others) attached together along their outer surfaces 122. It may be used by any of the methods described herein.

The above description of preferred embodiments should not be interpreted in a limiting manner since other variations, modifications, and refinements are also possible with the spirit and scope of the present invention. The scope of the invention is defined in the appended claims and their equivalents.

The invention claimed is:

1. A method of preparing a tooth for a dental procedure comprising the steps of: (A) removing a portion of a tooth to create a tooth abutment; (B) preparing a provisional restoration; (C) adhering material to the provisional restoration; (D) placing the provisional restoration on the tooth abutment; and (E) exerting pressure on the provisional restoration to pack the material into a sulcus associated with the tooth.

2. A method of preparing a tooth for a dental procedure as recited in claim 1, wherein the provisional restoration has a margin and the step of adhering material to the provisional restoration comprising the step of adhering material to the margin of the provisional restoration.

3. A method of preparing a tooth for a dental procedure comprising the steps of: (A) removing a portion of a tooth to create a tooth abutment; (B) preparing a provisional restoration; (C) placing a device for retracting gingival tissue away from a tooth around the tooth abutment, the device comprising a preformed integral closed loop of material sized and dimensioned to be packed into a sulcus associated with the tooth, the closed loop having an inner surface suitable for placement against the tooth and an outer surface suitable for placement against gingival tissue; and (D) packing the device into a sulcus associated with the tooth by placing the provisional restoration on the tooth abutment on top of the device and exerting pressure on the provisional restoration.

4. A method of preparing a tooth as recited in claim 3, further comprising, after the step of removing a portion of the tooth, the step of applying injection paste to the device before the device is placed around the tooth abutment.

5. A method of preparing a tooth as recited in claim 3, further comprising, alter the step of removing a portion of the tooth, the step of applying injection paste into the sulcus before the device is placed around the tooth abutment.

6. A method of preparing a tooth for a dental procedure comprising the steps of: (A) removing a portion of a tooth to create a tooth abutment; (B) preparing a provisional restoration having a margin; (C) placing a device for retracting gingival tissue away from a tooth around the tooth abutment by releasably adhering the device to the margin of the provisional restoration and then placing the provisional restoration on the tooth abutment, the device comprising a preformed integral closed loop of material sized and dimensioned to be packed into a sulcus associated with the tooth, the closed loop having an inner surface suitable for placement against the tooth and an outer surface suitable for placement against gingival tissue; and (D) packing the device into a sulcus associated with the tooth by exerting pressure on the provisional restoration.

7. A method of preparing a tooth as recited in claim 6, further comprising, after the step of removing a portion of the tooth, the step of applying injection paste to the device before the device is placed around the tooth abutment.

8. A method of preparing a tooth as recited in claim 6, further comprising, after the step of removing a portion of the tooth, the step of applying injection paste into the sulcus before the device is placed around the tooth abutment.

* * * * *